United States Patent [19]

Murai et al.

[11] 4,429,140

[45] Jan. 31, 1984

[54] PROCESS FOR PREPARING DIBENZYLIDENE SORBITOLS AND DIBENZYLIDENE XYLITOLS

[75] Inventors: Koichi Murai, Nagaokakyo; Toshiaki Kobayashi, Kyoto; Kango Fujitani, Uji, all of Japan

[73] Assignee: New Japan Chemical Co., Ltd., Kyoto, Japan

[21] Appl. No.: 336,376

[22] PCT Filed: May 1, 1981

[86] PCT No.: PCT/JP81/00105

§ 371 Date: Dec. 29, 1981

§ 102(e) Date: Dec. 29, 1981

[87] PCT Pub. No.: WO81/03331

PCT Pub. Date: Nov. 26, 1981

[51] Int. Cl.$^3$ ............................................. C07D 407/00
[52] U.S. Cl. ..................................................... 549/370
[58] Field of Search ......................................... 549/370

[56] References Cited

U.S. PATENT DOCUMENTS 3,721,682  3/1973  Murai et al. ........................ 549/364

4,267,110  5/1981  Uchiyama et al. ................. 549/370

FOREIGN PATENT DOCUMENTS 48-43748  2/1973  Japan.
49-14758  10/1974  Japan.

OTHER PUBLICATIONS

Chem. Abstracts 47:3235g.

*Primary Examiner*—Ethel G. Love
*Attorney, Agent, or Firm*—Larson and Taylor

[57] ABSTRACT

A process for preparing dibenzylidene sorbitols or dibenzylidene xylitols by reacting sorbitol or xylitol with a substituted or unsubstituted benzaldehyde or alkyl acetal derivative thereof in the presence of an acid catalyst, a hydrophobic organic solvent and a water-soluble organic polar solvent, the process being characterized by using the hydrophobic organic solvent in an amount sufficient to permit the resulting dibenzylidene sorbitols or dibenzylidene xylitols to separate out as crystals and capable of maintaining the reaction system in the form of a gel to solid phase and by conducting the reaction with forced agitation.

6 Claims, No Drawings

PROCESS FOR PREPARING DIBENZYLIDENE SORBITOLS AND DIBENZYLIDENE XYLITOLS

TECHNICAL FIELD

The present invention relates to a process for preparing dibenzylidene sorbitols and dibenzylidene xylitols, and more particularly to a process for preparing dibenzylidene sorbitol, dibenzylidene xylitol and their nuclear substitution compounds.

BACKGROUND ART

Dibenzylidene sorbitol, dibenzylidene xylitol and nuclear substitution compounds thereof have unique properties as additives and are used, for example, as transparency imparting agents for polypropylene resins, anti-rutting agents for asphalt pavements, precipitation preventing agents for preparing and storing coal-and-oil mixture fuels, flowability improving agents for PVC paste sols, flowability improving agents for FRP, excipients for pharmaceuticals, cosmetics and the like, marking agents, fuel solidifying agents, etc. Among the benzylidene sorbitol, benzylidene xylitol and nuclear substitution compounds thereof, especially the 1,3- and 2,4-substituted compounds represented by the following structural formula have the properties useful as such additives.

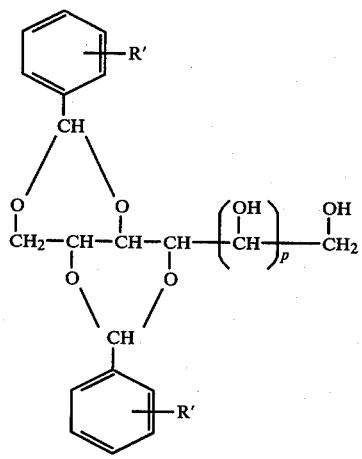

wherein $R'$ is an alkyl group, alkoxy group, halogen atom or nitro group, and $p$ is an integer of 1 or 0.

Accordingly it is important to prepare such 1,3- and 2,4-substituted compounds in high yields and with high selectivities.

Dibenzylidene sorbitol is usually produced by the dehydration condensation reaction of sorbitol and benzaldehyde. Processes have been developed in recent years for carrying out this reaction in the form of a slurry with use of cyclohexane and/or a saturated hydrocarbon having 6 to 10 carbon atoms in a large amount as the reaction medium (Published Examined Japanese Patent Applications No. 43748/1973 and No. 14758/1974). These processes utilize the properties of the reaction medium that it is azeotropic with water and free of gelation by the resulting benzilidene sorbitol. More specifically when the reaction medium of cyclohexane and/or saturated hydrocarbon with 6 to 10 carbon atoms is used, the water resulting from the reaction is continuously withdrawn from the system by an azeotropic phenomenon to promote the dehydration reaction, while the product separates out and disperses in the reaction medium in the form of pearl-like particles without gelling or solidifying the medium, permitting the reaction to proceed in the state of a slurry having a low viscosity. Accordingly the reaction can be carried out efficiently in a reactor equipped with a usual impeller mixer while assuring good dispersion of the charge, consequently giving the desired product in a yield of at least about 70% within a relatively short period of time, i.e. about 5 to 7 hours. For the reaction medium to be serviceable as a dispersing agent in the processes, the medium is limited to cyclohexane and/or saturated hydrocarbons having 6 to 10 carbon atoms which will not be gelled or solidified by the resulting benzylidene sorbitol. Furthermore it is critical that the medium be used in a large amount to maintain the reaction system in the form of a slurry as mentioned above.

Our research has revealed the totally unexpected fact that although the reaction system becomes a gel to solid phase when cyclohexane and/or saturated hydrocarbon are/is used in a small amount, the reaction system, if forcibly agitated, affords in a high yield and with a high selectivity the desired compound, especially 1,3- and 2,4-substituted compounds having the above-mentioned unique properties as additives. More specifically when a system comprising sorbitol or xylitol, a benzaldehyde or an alkyl acetal derivative thereof, a catalyst and a water-soluble polar solvent according to the conventional process is subjected to reaction with addition of a small amount of cyclohexane or the like, the resulting dibenzylidene sorbitols or dibenzylidene xylitols separate out as crystals while gelling or solidifying the reaction system to render the cyclohexane or the like no longer serviceable as the dispersing medium as used in the conventional process. Surprisingly, however, when the reaction system in the form of a gel to solid phase is forcibly agitated, the system gives in high yields and with high selectivities dibenzylidene sorbitols or dibenzylidene xylitols which have the aforementioned unique properties as additives. Our research has further revealed that such a result is achieved not only when using cyclohexane, saturated hydrocarbons, etc. which will not be gelled by dibenzylidene sorbitols or dibenzylidene xylitols but also when using hydrophobic solvents alike which will inherently be gelled or solidified by such compounds. The present invention has been accomplished based on such novel findings.

DISCLOSURE OF THE INVENTION

The present invention relates to a process for preparing dibenzylidene sorbitols or dibenzylidene xylitols by reacting sorbitol or xylitol with a substituted or unsubstituted benzaldehyde or alkyl acetal derivative thereof in the presence of an acid catalyst, a hydrophobic organic solvent and a water-soluble organic polar solvent, the process being characterized by using the hydrophobic organic solvent in an amount sufficient to permit the resulting dibenzylidene sorbitols or dibenzylidene xylitols to separate out as crystals and capable of maintaining the reaction system in the form of a gel to solid phase and by conducting the reaction with forced agitation.

The reaction of this invention, although effected in the state of a gel to solid phase, gives the desired product in a high yield of at least about 80% and with a high purity of at least about 90% at all times. Moreover the reaction can be carried out within as short a period as about 3 hours, whereas the foregoing conventional processes require 5 to 7 hours. This is very inconceivable in chemistry in which it is generally thought that the reaction in a gel to solid phase usually involves reduced dispersion and reduced reactivity of the starting material, resulting in lower yield and selectivity and necessitating a prolonged period of time. The invention has other advantages in that the process can be practiced with use of a compact reactor and ensures savings in energy.

According to the invention, sorbitol or xylitol is usable in any of various forms, i.e. in the form of a dilute or concentrated aqueous solution or a solid in which it is usually available commercially.

The benzaldehydes to be reacted with sorbitol or xylitol are not particularly limited and are a wide variety of those presently used for producing the dibenzylidene sorbitols or dibenzylidene xylitols having the aforementioned unique properties as additives.

Preferred examples are substituted or unsubstituted benzaldehydes represented by the following formula

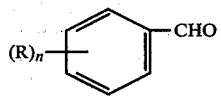

wherein R is a hydrogen atom, lower alkyl group, lower alkoxy group, halogen atom or nitro group, and n is an integer of 1 to 3.

In addition to benzaldehydes, alkyl acetal derivatives thereof are also usable in this invention. Such alkyl acetal derivatives can be prepared by a usual process, for example, by reacting benzaldehydes with a lower alcohol having about 1 to 5 carbon atoms or a lower alkyl ester of o-formic acid. The benzaldehyde or alkyl acetal derivative thereof is used in an amount of about 1 to 2.8 moles, preferably about 1.5 to 2.5 moles, per mole of sorbitol or xylitol.

Acid catalysts usable for this invention are any of those usually used for producing benzylidene sorbitols. Typical of such acid catalysts are, for example, sulfuric acid, p-toluenesulfonic acid, phosphoric acid, hydrochloric acid, zinc chloride, $C_{2-12}$ alkyl benzenesulfonic acids, G-acid, L-acid, etc. The acid catalyst is used usually in an amount of about 0.05 to 10 parts by weight, preferably about 0.2 to 3 parts by weight, per 100 parts by weight of sorbitol or xylitol, and a benzaldehyde or alkyl acetal derivative thereof (hereinafter referred to simply as "materials").

According to the invention, hydrophobic organic solvents serve to cause the dibenzylidene sorbitols or dibenzylidene xylitols which are formed with the progress of the reaction to separate out as crystals. The solvents also perform the function of maintaining the reaction system in the form of a gel to solid phase but do not serve the function of the dispersing medium used in the conventional processes. Preferably such hydrophobic organic solvents are azeotropic with water from the viewpoint of removal of water from the reaction system. Useful hydrophobic organic solvents are not limited to those which will not be gelled or solidified by the product; solvents which will be gelled or solidified by the products are also usable if they dissolve the benzaldehydes used as materials, are hydrophobic but will not be easily decomposed by the acid catalyst. Examples of useful solvents which are free of gelation or solidification by the product are cyclohexane, cyclohexanes substituted with lower alkyl such as methylcyclohexane, ethylcyclohexane, etc., chain saturated hydrocarbons having 6 to 16 carbon atoms such as n-hexane, kerosene, heptane, octane, decane, dodecane, etc., carbon tetrahalides such as carbon tetrachloride, etc. These solvents are used singly, or at least two of them are usable in admixture. Examples of useful solvents which will be gelled or solidified by the product are aromatic hydrocarbons such as benzene, toluene, xylene, ethylbenzene, mesitylene, cumene, pseudocumene, diphenyl, etc.; hydrocarbon halides such as chloroform, 1,2-dichloroethane, 1,2-dichloropropane, 1-chloropropane, 1-chlorobutane, 1-chloro-1-methylpropane, trichloroethylene, dichloroethylene, chlorobenzene, etc.; ethers such as isopropyl ether, isoamyl ether, methyl butyl ether, 1,2-dimethoxyethane, 1,2-diethoxyethane, anisole, phenetole, diphenyl ether, etc.; nitro compounds such as nitromethane, nitrobenzene, etc.; esters such as methyl benzoate, butyl benzoate, etc.; ketones such as di-t-butyl ketone; decalin; etc. These can be used singly, or at least two of them are usable in admixture. These hydrophobic organic solvents are used in small amounts, but too small an amount of such a solvent, if used, will not permit the desired product to separate out as crystals, turning the reaction system to a syrup-like consistent liquid and failing to afford the desired product in a high yield and with a high selectivity. Accordingly the hydrophobic organic solvent is used in an amount sufficient to cause the product to separate out as crystals. This amount is usually at least about 40 parts by weight, preferably at least about 45 parts by weight, per 100 parts by weight of the materials, although variable in accordance with the kinds of the materials, the kind and amount of the water-soluble organic polar solvent, the reaction conditions, etc. From the viewpoint of reaction efficiency, the hydrophobic organic solvent is used in such an amount as to maintain the reaction system in the form of a gel to solid phase. Although this amount is also variable according to the kinds of the materials used, the reaction conditions, the kind and amount of the water-soluble organic polar solvent, etc., the amount is generally up to about 200 parts by weight, preferably up to about 150 parts by weight, per 100 parts by weight of the materials, whereby the reaction can be conducted in a satisfactory gel to solid phase.

It is thought that the water-soluble organic polar solvent used in this invention provides the site of reaction by dissolving the materials, namely sorbitol or xylitol and benzaldehydes. In fact, the reaction almost fails to proceed in the absence of this solvent. Preferred water-soluble organic polar solvents are protic solvents including alcohols such as methanol, ethanol, propanol, isopropanol, butanol, t-butanol, n-amyl alcohol, isoamyl alcohol, etc.; and glycol ethers such as ethylene glycol monomethyl ether, monoethyl ether, monopropyl ether and monobutyl ether, etc. Also usable are N,N-dimethylformamide, N,N-dimethylacetamide, N-methylpyrrolidone, sulfolane, dimethylsulfolane, dioxane, cyclohexanone, diglyme and like aprotic solvents. The protic solvent and the aprotic solvent can be used in combination. Such a water-soluble organic polar solvent is used usually in an amount of about 5 to 300 parts by weight per 100 parts by weight of the materials, although the amount is variable in accordance with the kinds of the materials used, the reaction conditions, etc. In the case of the protic solvent, the amount is preferably about 50 to 300 parts by weight, more preferably about 80 to 200 parts by weight, per 100 parts by weight of the materials. In the case of the aprotic solvent, the amount is preferably about 5 to 50 parts by weight, more preferably about 7 to 40 parts by weight, per 100 parts by weight of the material.

Generally the present invention is practiced in the following manner. Since the reaction of the process of the invention is conducted in a gel to solid phase, usual impeller mixers are not usable, and there is the need to use a reactor equipped with a forced agitator, such as a kneader, a versatile mixer, etc. Also usable are rotary press drier for slurry, etc. The reactor is preferably one having a gas inlet and a condenser equipped with a decanter. First, the materials (sorbitol or xylitol, and a benzaldehyde or alkyl acetal derivative thereof), an acid catalyst, a hydrophobic organic solvent and a water-soluble organic polar solvent are charged into the reactor. These may be charged in any order desired. Preferably the air in the reactor is replaced by an inert gas, such as nitrogen gas.

The mixture placed in is then agitated for reaction. The reaction temperature is generally about 30° to 180° C., preferably about 50° to 150° C., although variable in accordance with the kinds and amounts of the hydrophobic organic solvent and the water-soluble organic polar solvent, etc. With the progress of the reaction, the water resulting from the condensation reaction forms an azeotropic mixture with the hydrophobic organic solvent and is distilled off from the system, or the water is distilled off according to vapor-liquid equilibrium. When an alkyl acetal derivative of a benzaldehyde is used as one of the materials, the alcohol released by acetal exchange reaction also forms an azeotropic mixture with water and/or the hydrophobic organic solvent and is thereby removed from the system, or is distilled off according to vapor-liquid equilibrium. The water-soluble polar solvent also is partly removed similarly. These fractions are condensed by the condenser, and the condensate is separated into a hydrophobic organic solvent layer and an aqueous layer. The solvent layer can be recycled through the reaction system. The aqueous layer is withdrawn from the reactor. As the reaction proceeds, the resulting product separates out as crystals, while the hydrophobic organic solvent and water-soluble organic polar solvent in the reactor become gelled or solidified. The hydrophobic organic solvent, when free of gelation or solidification by the product, is absorbed or adsorbed by the product. Thus in the initial or intermediate stage of the reaction, the reaction system becomes a gel to solid phase, which, when forcibly agitated continuously, permits the reaction to proceed further. Generally the reaction is completed within a short period of time, i.e. about 3 hours.

The reaction mixture obtained in the form of a gel to solid phase is treated by a usual method, for example, with an aqueous alkali hydroxide solution to neutralize the acid catalyst, then washed with hot water and/or an aqueous solution of surfactant to remove the unreacted materials, intermedate and organic polar solvent, and thereafter filtered. The desired product is obtained after drying.

The present invention will be described in greater detail with reference to the following examples and comparison examples, in which the purity and composition of the reaction products are determined by chromatography.

EXAMPLES 1-7

Sorbitol and benzaldehyde in a combined amount of 100 parts by weight and in the mole ratio listed in Table 1 are placed into a kneader having a thermometer, nitrogen inlet and condenser having a decanter. Subsequently cyclohexane and methanol in the amounts listed in Table 1 and 0.5 part by weight of 98% sulfuric acid serving as a catalyst are placed into the kneader. The materials are reacted at 78° to 82° C. in nitrogen atmosphere. The water formed is distilled off as an azeotropic mixture along with cyclohexane and methanol. The cyclohexane condensed and separated off by the condenser is recycled through the reaction system, while the aqueous layer is withdrawn from the system. In this way, the materials are reacted for 3 hours, giving a reaction mixture which appears semisolid to powdery. The composition of the reaction mixture is analyzed with the result shown in Table 1. The reaction mixture is neutralized with an aqueous KOH solution, washed with hot water and filtered to obtain a product upon drying. Table 1 also shows the yield of the product.

Comparison Examples 1-3

The same reaction procedure as in Examples 1-7 is repeated with the exception of using sorbitol, benzaldehyde, cyclohexane and methanol in the charge mole ratios or amounts listed in Table 1. Table 1 shows the appearance and composition of each reaction mixture obtained by the three-hour reaction, and the yield of the product obtained by treating the mixture in the same manner as above.

TABLE 1

|  | Cyclohexane (wt. parts) | Sorbitol/ benzaldehyde (charge mol ratio) | Methanol (wt. parts) | Appearance of reaction mixture | Composition of reaction mixture (wt. %) | | | | Yield (%) |
| --- | --- | --- | --- | --- | --- | --- | --- | --- | --- |
|  |  |  |  |  | Sorbitol | MBS[1] | DBS[2] | Isomers[3] |  |
| Comp. Ex. 1 | 0 | 1.0/2.0 | 150 | Syrup | 7.5 | 19.2 | 52.5 | 20.8 | 61 |
| Comp. Ex. 2 | 25 | 1.0/2.0 | 120 | " | 3.2 | 12.6 | 72.5 | 11.7 | 80 |
| Example 1 | 43 | 1.2/2.0 | 120 | Powder | 0.3 | 2.3 | 94.9 | 2.5 | 95 |
| Example 2 | 55 | 1.0/2.5 | 180 | " | 0.3 | 2.0 | 97.5 | 0.2 | 96 |
| Example 3 | 70 | 1.0/1.8 | 150 | " | 0.3 | 1.5 | 98.0 | 0.3 | 97 |
| Example 4 | 100 | 1.0/2.0 | 100 | " | 0.4 | 1.8 | 97.5 | 0.3 | 97 |
| Example 5 | 120 | 1.0/2.0 | 300 | Semisolid | 1.0 | 2.8 | 96.0 | 0.2 | 94 |
| Example 6 | 150 | 1.0/2.0 | 60 | " | 2.5 | 6.2 | 91.0 | 0.3 | 90 |
| Example 7 | 200 | 1.0/2.0 | 200 | " | 4.0 | 5.0 | 92.5 | 0.5 | 80 |
| Comp. Ex. 3 | 250 | 1.0/2.0 | 120 | Slurry | 7.2 | 9.0 | 83.2 | 0.6 | 75 |

[1]MBS: monobenzylidene sorbitol
[2]DBS: dibenzylidene sorbitol (1,3- and 2,4-compounds)
[3]Isomers: extract obtained by Soxhlet extraction method with use of cyclohexane Table 1 reveals that the reaction, when conducted in a gel to solid phase, gives the desired product in a high yield with a high purity. The result of Comparison Example 1 indicates that the use of the hydrophobic organic solvent is critical.

Comparison Example 4

The same reaction procedure as in Example 1 is repeated with the exception of using xylitol (1 mole) and benzaldehyde dimethyl acetal (2 moles) in a combined amount of 100 parts by weight, 100 parts by weight of methanol and 1.0 part by weight of 98% concentrated sulfuric acid. The reaction is conducted for 6 hours, giving a reaction mixture which appears to be a consistent uniform liquid. When neutralized, washed with hot water, filtered and dried, the mixture affords a solid product in a yield as low as 52%. The product contains about 20% of isomers soluble in cyclohexane.

EXAMPLE 8

Sorbitol (28.8 g), 31.5 g of benzaldehyde, 0.5 g of 50% sulfuric acid, 5 ml of N,N-dimethylformamide and 70 ml of cyclohexane are placed into the kneader used in Example 1. The materials are reacted in nitrogen atmosphere at 82° C. with forced agitation. The cyclohexane is distilled off as an azeotropic mixture with water, then condensed and separated off by the condenser, and thereafter recycled through the reaction system. The reaction system becomes a semisolid phase with the progress of the reaction and appears powdery in 3 hours. The reaction mixture is cooled, neutralized with an aqueous KOH solution, washed with hot water and filtered. The product, when dried, gives 50 g of 1,3- and 2,4-dibenzylidene sorbitols. Yield: 95%. Purity: 99%.

Comparison Example 5

The same reaction procedure as in Example 8 is repeated without using any N,N-dimethylformamide. However, the reaction system becomes neither gelled nor semisolidified but separates into two layers, failing to afford the desired dibenzylidene sorbitol since hardly any reaction occurs.

EXAMPLE 9

The same reaction procedure as in Example 8 is repeated except that benzaldehyde is replaced by 60 g of 2,4,5-trimethylbenzaldehyde dimethyl acetal. The methanol formed is distilled off. The materials are reacted for 3 hours, affording a powdery reaction mixture, which is similarly after-treated, whereby di-(trimethylbenzylidene)sorbitol is obtained in a yield of 93% with a purity of 98%.

EXAMPLE 10

A semisolid reaction mixture is obtained in the same manner as in Example 8 with the exception of using 26.8 g of sorbitol, 35.0 g of p-tolualdehyde, 0.4 g of p-toluenesulfonic acid, 85 ml of n-heptane and 200 ml of n-butanol and reacting the materials at 95° C. The mixture is similarly after-treated to give di-(p-methylbenzylidene)sorbitol in a yield of 96% with a purity of 97%.

EXAMPLE 11

The reaction procedure of Example 8 is repeated in the same manner with the exception of using 26.8 g of sorbitol, 48.0 g of p-isopropylbenzaldehyde, 1.0 g of $C_9$ alkylbenzenesulfonic acid, 9 ml of dimethylsulfoxide, 120 ml of benzene and 100 ml of isopropanol. The reaction is conducted in a semisolid phase for 3 hours, giving di-(p-isopropylbenzylidene)sorbitol in a yield of 93% with a purity of 95%.

EXAMPLE 12

A powdery reaction mixture is obtained in the same manner as in Example 8 with the exception of using 24.0 g of xylitol, 41.5 g of p-chlorobenzaldehyde, 0.5 g of 50% sulfuric acid, 60 ml of trichloroethylene and 18 ml of dioxane. The mixture is similarly after-treated, affording di-(p-chlorobenzylidene)xylitol in a yield of 92% with a purity of 97%.

EXAMPLE 13

The same procedure as in Example 8 is repeated with the exception of using 26.8 g of sorbitol, 39.5 g of 2,4-dimethylbenzaldehyde, 50 ml of cyclohexane, 0.4 g of p-toluenesulfonic acid, 30 ml of anisole and 100 ml of ethanol. The reaction is conducted for 2.5 hours, giving a powdery reaction mixture, which is similarly after-treated to obtain di-(2,4-dimethylbenzylidene)sorbitol in a yield of 93% with a purity of 98%.

EXAMPLE 14

A semisolid reaction mixture is obtained in the same manner as in Example 8 with the exception of using 26.8 g of sorbitol, 39.3 g of p-ethylbenzaldehyde, 1.2 g of dodecylbenzenesulfonic acid, 5.0 ml of N,N-dimethlformamide and 80 ml of nitrobenzene. The mixture is thereafter similarly treated to give di-(p-ethylbenzylidene)sorbitol in a yield of 96% with a purity of 95%. The reaction time is 2.5 hours.

EXAMPLE 15

The same procedure as in Example 8 is repeated with the exception of using 30.3 g of sorbitol, 45.7 g of p-methoxybenzaldehyde, 1.0 g of p-toluenesulfonic acid, 8 ml of cyclohexanone, 175 ml of $C_8$–$C_{10}$ saturated hydrocarbons and 8 ml of amyl alcohol. The materials are reacted for 3 hours, giving a semisolid reaction mixture. The mixture is similarly treated thereafter, affording di-(p-methoxybenzylidene)sorbitol in a yield of 92% with a purity of 99%.

EXAMPLE 16

The same procedure as in Example 8 is repeated with the exception of using 30.3 g of sorbitol, 44.0 g of p-nitrobenzaldehyde, 1.5 g of p-toluenesulfonic acid, 5 ml of N-methylpyrrolidone, 150 ml of methylcyclohexane and 20 ml of ethylene glycol monomethyl ether. The materials are reacted for 2.7 hours, giving a semisolid paste. The paste is thereafter treated similarly to afford di-(p-nitrobenzylidene)sorbitol in a yield of 91% with a purity of 97%.

We claim:

1. A process for preparing a 1,3:2,4-dibenzylidene sorbitol or 1,3:2,4-dibenzylidene xylitol comprising reacting sorbitol or xylitol with a substituted or unsubstituted benzaldehyde or alkyl acetal derivative thereof in the presence of an acid catalyst, a hydrophobic organic solvent, and a water-soluble organic polar solvent, said hydrophobic solvent being selected from the group consisting of cyclohexane, a cyclohexane substituted with lower alkyl, a chain saturated hydrocarbon having 6 to 16 carbon atoms, a carbon tetrahalide, an aromatic hydrocarbon, a hydrocarbon halide, an ether, a nitro compound, an ester, a ketone and decalin, said water-soluble organic polar solvent being selected from the group consisting of an alcohol, a glycol ether, N,N-dimethylformamide, N,N-dimethylacetamide, N-methylpyrrolidone, sulfolane, dimethylsulfolane, dioxane, cyclohexanone and diglyme, said hydrophobic organic solvent being used in an amount sufficient to permit the resulting 1,3:2,4-dibenzylidene sorbitol or 1,3:2,4-dibenzylidene xylitol to separate out as crystals and sufficient to maintain the reaction system in the form of a gel to solid phase, and said reaction being conducted with forced agitation.

2. A process as defined in claim 1 wherein the hydrophobic organic solvent is one which is free from gelation by the resulting dibenzylidene sorbitols or dibenzylidene xylitols.

3. A process as defined in claim 2 wherein the hydrophobic organic solvent is at least one of cyclohexanes having or not having a lower alkyl substituent, chain saturated hydrocarbons having 6 to 16 carbon atoms and carbon tetrahalides.

4. A process as defined in claim 1 wherein the hydrophobic organic solvent is one which is subject to gelation by the resulting dibenzylidene sorbitols or dibenzylidene xylitols.

5. A process as defined in claim 1 wherein the amount of the hydrophobic organic solvent sufficient to permit the resulting dibenzylidene sorbitols or dibenzylidene xylitols is at least 40 parts by weight per 100 parts by weight of the materials.

6. A process as defined in claim 1 wherein the amount of the hydrophobic organic solvent capable of maintaining the reaction system in the form of a gel to solid phase is up to 200 parts by weight per 100 parts by weight of the materials.

* * * * *